(12) United States Patent
Richart

(10) Patent No.: US 11,931,190 B2
(45) Date of Patent: Mar. 19, 2024

(54) DEVICE FOR HOLDING AND RELEASING AN OBJECT, CORRESPONDING ASSEMBLY AND RELEASE METHOD

(71) Applicant: SELENIUM MEDICAL, La Rochelle (FR)

(72) Inventor: Olivier Richart, Le Bois Plage en Re (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 17/054,099

(22) PCT Filed: May 20, 2019

(86) PCT No.: PCT/FR2019/051142
§ 371 (c)(1),
(2) Date: Nov. 9, 2020

(87) PCT Pub. No.: WO2019/220067
PCT Pub. Date: Nov. 21, 2019

(65) Prior Publication Data
US 2021/0212788 A1    Jul. 15, 2021

(30) Foreign Application Priority Data

May 18, 2018   (FR) ...................... 1854199

(51) Int. Cl.
*A61B 50/30*   (2016.01)
*A61B 17/86*   (2006.01)

(52) U.S. Cl.
CPC ............ *A61B 50/30* (2016.02); *A61B 17/865* (2013.01)

(58) Field of Classification Search
CPC .................. A61B 50/30; A61B 17/865; A61B 2050/0059; A61B 50/20; A61C 8/0087
See application file for complete search history.

(56) References Cited

U.S. PATENT DOCUMENTS 5,024,326 A *  6/1991  Sandel ................. A61B 50/362
                                                      D24/227
2004/0065572 A1* 4/2004 Anthony ............ A61B 50/3001
                                                      206/366

(Continued)

FOREIGN PATENT DOCUMENTS

DE       202007004638       6/2007
DE       202007004638 U1 *  7/2007 ............. A61B 17/86

(Continued)

OTHER PUBLICATIONS

International Search Report dated Sep. 10, 2019.
Search Report dated Jan. 30, 2019.

*Primary Examiner* — Ernesto A Grano
*Assistant Examiner* — Symren K Sanghera
(74) *Attorney, Agent, or Firm* — IPSILON USA, LLP

(57) ABSTRACT

A device for holding and releasing an object (2), such as a medical implant, is proposed. The device comprises two hook systems (11, 12) to which said object (2) is able to be coupled so as to allow said hook systems (11, 12) to jointly hold said object (2). Said hook systems (11, 12) are configured such that, in the state in which said object (2) is coupled to said hook systems (11, 12), at least one of the hook systems (11, 12) is subjected to a return force (F11, F12) that makes it possible to keep the object (2) coupled to said hook systems (11, 12). Also proposed are a corresponding assembly and a corresponding releasing method.

14 Claims, 5 Drawing Sheets

(56) References Cited

U.S. PATENT DOCUMENTS

| | | | | |
|---|---|---|---|---|
| 2008/0230423 A1* | 9/2008 | Loeffler | ................. | A61B 90/90 |
| | | | | 606/300 |
| 2013/0103150 A1* | 4/2013 | Turner | ................. | A61B 17/865 |
| | | | | 340/10.1 |
| 2013/0105577 A1* | 5/2013 | Hildreth | ............. | A61B 17/7001 |
| | | | | 206/307 |
| 2014/0042050 A1* | 2/2014 | Richart | ................. | A61F 2/0095 |
| | | | | 206/438 |
| 2016/0051297 A1* | 2/2016 | Steffensmeier | ...... | A61B 17/808 |
| | | | | 606/86 B |
| 2016/0074118 A1* | 3/2016 | Tuechsen | ............... | A61B 50/30 |
| | | | | 206/572 |
| 2016/0331483 A1* | 11/2016 | Richart | .................. | A61B 50/30 |
| 2017/0354478 A1* | 12/2017 | Adams | ................... | A61B 90/90 |
| 2021/0177471 A1* | 6/2021 | Detweiler | ............ | A61B 17/808 |

FOREIGN PATENT DOCUMENTS

| | | |
|---|---|---|
| DE | 202014100438 | 4/2014 |
| WO | 2015179931 | 12/2015 |
| WO | WO-2015179931 A1 * 12/2015 | ........... A61B 17/865 |

* cited by examiner

DEVICE FOR HOLDING AND RELEASING AN OBJECT, CORRESPONDING ASSEMBLY AND RELEASE METHOD

RELATED APPLICATION

This application is a National Phase of PCT/FR2019/051142 filed on May 20, 2019, which claims the benefit of priority from French Patent Application No. 18 54199, filed on May 18, 2018.

FIELD OF THE INVENTION

The present invention relates in general to a device for holding an object, such as a medical implant, and for releasing said object from this device. The invention also relates to a corresponding assembly and a corresponding method for releasing an object.

PRIOR ART

Devices for holding an object, also known as grippers, which make it possible to couple a medical implant to said device, are known from the prior art. The operator can grasp the device and deactivate the coupling of the object to the device in order to take hold of the implant.

The documents WO 2015/179931, DE 20 2014 100438 U1, DE 20 2007 004638 and US 2013/103150 A1 describe such grippers.

It is desirable to be able to provide other object holding devices in which the object can be held reliably while allowing it to be released easily from the device and while limiting the risk of accidental releasing.

SUMMARY OF THE INVENTION

To this end, a device for holding and releasing an object, such as a medical implant, is proposed, characterized in that the device comprises two hook systems to which said object is able to be coupled so as to allow said hook systems to jointly hold said object, said hook systems being configured such that, in the state in which said object is coupled to said hook systems, at least one of the hook systems is subjected to a return force that makes it possible to keep the object coupled to said hook systems.

The return force exerted by at least one of the hook systems on the object makes it possible to keep the object in contact not only with said hook system but also with the other hook system.

Thus, the object remains held reliably in the device by the hook systems, in particular in the absence of external loading moving the or one of the hook systems into the releasing position, or in the absence of voluntary loading on the object, such as pivoting loading on the part of the operator for pivoting the object in the releasing direction with respect to the hook systems.

The device can be housed in packaging or double packaging as described in the international application WO2014188142, the content of which is incorporated into the present application by reference, or the international application WO2018078242, the content of which is incorporated into the present application by reference.

The device may also have one or more of the following features in any technically admissible combination.

According to one particular feature, in the state in which said object is coupled to said hook systems, with each of said hook systems being subjected to a return force, said hook systems are configured such that the return force to which one of said hook systems is subjected tends to move it in the opposite direction to the direction of the return force to which the other hook system is subjected, the object being kept coupled to said hook systems under the effect of the return forces applied in opposite directions to the object by said hook systems.

According to one particular aspect, each hook system tends to return the object in the opposite direction to the other hook system.

In particular, each hook system tends to return the object next to the arm of said hook system.

According to one particular feature, at least one, preferably each, of the hook systems is configured to be able to be moved with respect to the other hook system into a position, referred to as the releasing position, that makes it possible to release the object from the hook systems.

In particular, in the releasing position, the return force(s) previously applied to the hook system(s) is/are reduced or eliminated, thereby making it easier to release the object from the hook systems.

According to one particular feature, at least one, preferably each, of the hook systems comprises an arm that is provided with at least one hook, and said or each arm is movable, preferably by bending or elastic deformation, so as to allow the corresponding hook system to be moved with respect to the other hook system.

According to one embodiment, the movement of the hook systems into the releasing position is effected in the direction of a movement of the arms of the hook systems toward one another.

According to one particular feature, the device comprises a body to which each hook system is coupled.

According to one particular feature, each hook system has at least one hook that exhibits a passage through which at least a part of said object is able to extend. In particular, said passage of said at least one hook of each hook system exhibits a passage axis along which at least a part of said object is able to extend.

According to one particular feature, the hooks are distributed, in the state in which the object is coupled to said hook systems, at different positions along said passage axis.

Said hooks are thus disposed so as to hook (or partially surround) different parts or portions of the object.

In other words, each hook system comprises at least one hook, which, in the state in which the object is coupled to said hook systems, is spaced apart from said at least one hook of the other hook system along an axis parallel to the axis of the housing of the body intended to receive a part of the object.

The passage which is delimited by each hook and through which the object extends, in the state in which it is coupled to the hook systems, has a passage axis that is substantially parallel to the axis of the housing provided in the body and intended to receive at least a part of the object.

Advantageously, in the case of an embodiment in which the arm of the coupling system is moved by bending (elastic deformation) about a corresponding axis, said passage axis of the hook is transverse, preferably orthogonal, to the axis of bending of the or each coupling system.

According to one particular feature, said or each hook system is movable by bending about an axis orthogonal to said passage axis. In particular, said axis about which said or each hook system is movable is also orthogonal to the mean plane of the body or of the cover.

According to one particular feature, said at least one hook of each hook system has a hook opening zone configured so as to allow said object to be released through said hook opening zone by said object being pivoted about an axis orthogonal to the passage axis. According to one particular aspect, the pivoting axis for releasing the object is also parallel to the mean plane of the body or of the cover.

According to one particular feature, one of the hook systems comprises an additional hook, through which at least a part of said object is able to extend, said at least one hook of the other hook system being able to extend, in the state in which the object is coupled to the hook systems, between the two hooks of said hook system.

According to one particular aspect, the passage axis of the exterior additional hook is coaxial with the other hook of the corresponding hook system.

In the state in which the object is coupled to the hook systems, said hooks are distributed at different positions along the passage axis of the hooks.

According to one particular feature, at least one of the hooks has an end portion that extends in such a way that, when the object is coupled to the hook systems by being subjected to the return force of the hook system or each of the hook systems, said end portion opposes releasing of the object by movement in translation in a direction contained in a plane orthogonal to the axis along which the object extends in the state in which the object is held by said hook systems.

According to one particular feature, the end portion of this hook comprises a ramp that makes it possible to release the object by pivoting the object about an axis orthogonal to the axis along which said object is held by the hook systems.

According to one particular feature, the hook systems are configured so as to allow the object to be released by pivoting the object about an axis orthogonal to the axis along which said object is held by the hook systems.

According to one particular feature, with each hook having an opening, referred to as the insertion/releasing opening, defined between the base of the hook and the free end of the curved part thereof, the opening of at least one, some, or each of the hooks has more or less the same orientation as the opening of at least one, some, or each of the other hooks of the hook systems.

In other words, each hook has a coupling part that partially surrounds the object in the state in which said object is coupled to the hook systems. Each hook also has an open part. This open part corresponds to the space left free between the free end of the coupling part and the start of the coupling part that forms the connection between the arm of the coupling system and the corresponding coupling part.

This open part of the hook (that is to say the insertion/releasing opening) forms a radial opening with respect to the passage axis which is defined by the hook and along which the object extends. The object can be removed from the hook through this radial opening, in particular when this object is pivoted about an axis transverse to the passage axis of the hook.

According to one particular aspect, the insertion/releasing opening of each hook is open in a direction transverse to the passage axis of the hook and to the pivoting axis of the implant that allows it to be released by passing through said insertion/releasing opening.

The distribution of the hooks at different axial positions with respect to the passage axis, in the state in which the object is coupled to the hook systems, means that the insertion/releasing openings thereof are also distributed at different axial positions.

According to one particular feature, the support is phosphorescent or luminescent so as to be visible in the dark, in particular in an operating room environment.

According to one particular feature, the device also comprises a cover mounted so as to slide between a position, referred to as the concealing position, which at least partially conceals the hook systems, and another position, referred to as the position for accessing the hook systems, which allows the operator to move the hook systems.

According to one particular feature, the cover is configured such that, in the concealing position, the length of the object, that is to say at least the opposite ends thereof, remains visible.

The invention also relates to an assembly comprising a device as set out above and an object held by said hook systems.

The assembly may also have one or more of the following features in any technically admissible combination.

According to one particular feature, said object, preferably a medical implant, comprises an elongate screw body and a screw head, the hook systems engaging with the elongate screw body.

According to one particular aspect, the screw head has a diameter greater than the screw body, making it possible for said screw to butt against a hook, in particular the outermost hook of the device.

According to one particular feature, the end of the screw body is contained in a housing provided in a body of the device.

Advantageously, the axis of this housing is substantially parallel to or coaxial with the passage axis of the hooks in the state in which the screw is coupled to the hook systems.

The invention also relates to a method for releasing an object coupled to an assembly as set out above, said method comprising the following steps:
when a cover is present, moving the cover so as to allow access to the hook systems and/or to uncover a part of the object previously concealed by the cover;
releasing the object by:
 i) moving at least one, preferably each, of the hook systems by applying a force to at least one, preferably each, of the hook systems in a direction opposite to the return force of said hook system,
 or
 ii) pivoting the object about an axis transverse to the axis, referred to as the passage axis, along which the object extends, the pivoting being effected preferably with the aid of a tool coupled to the object.

Also proposed is a device for holding and releasing an object, such as a medical implant, characterized in that the device comprises two hook systems with which said object is able to be coupled in order to be held, said hook systems being configured such that, in the state in which said object is coupled to said hook systems, each hook system is subjected to a return force that tends to move it in the opposite direction to the direction of the return force to which the other hook system is subjected, the object being kept coupled to said hook systems under the effect of the return forces applied in opposite directions to the object by said hook systems.

BRIEF DESCRIPTION OF THE DRAWINGS

Further features and advantages of the invention will become more apparent from the following description, which is purely by way of nonlimiting illustration and should be read with reference to the appended drawings, in which.

DETAILED DESCRIPTION

Figure 1:
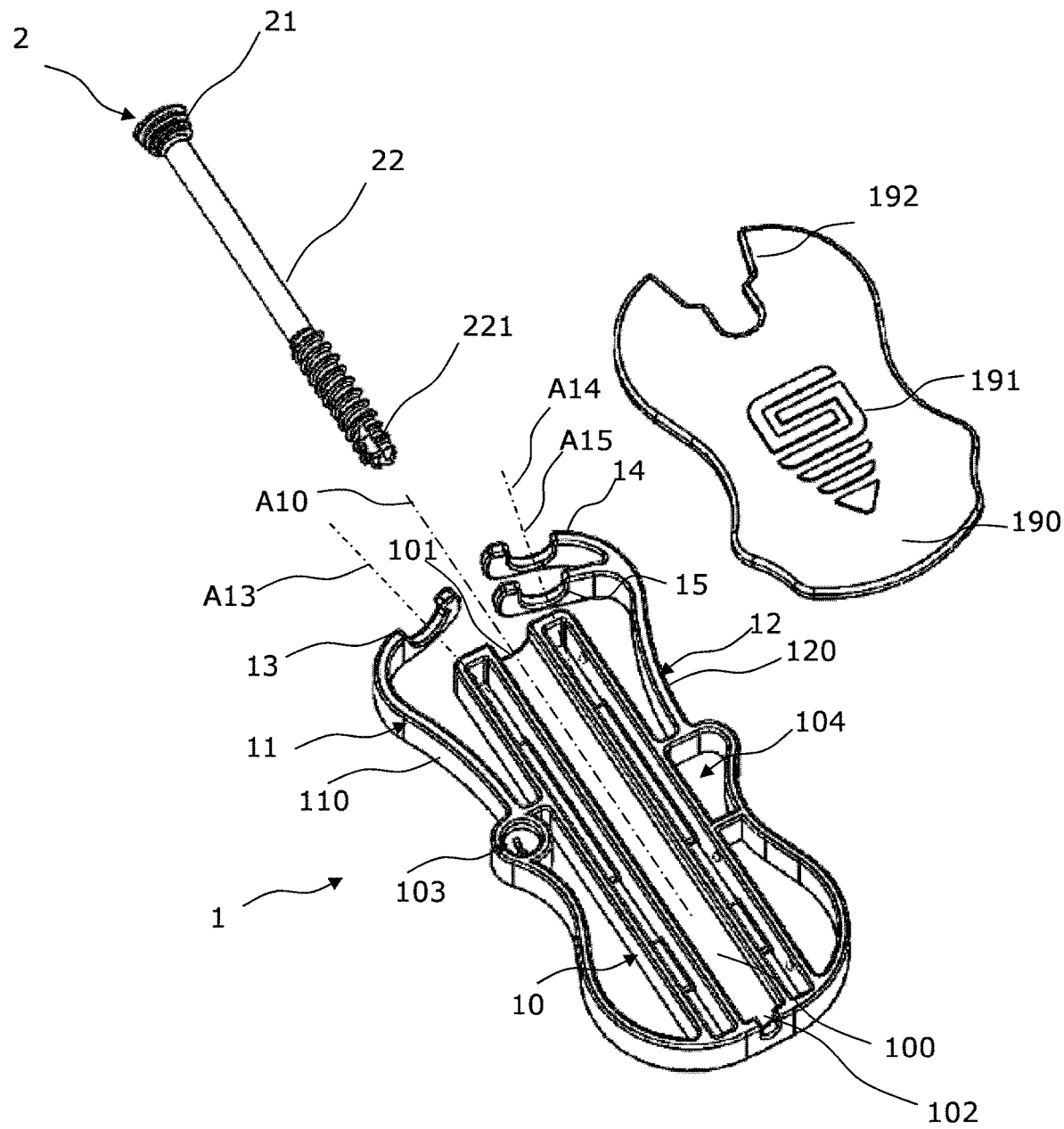
FIG. 1 is an exploded view of an assembly comprising a holding device and a medical implant according to one embodiment of the invention.

The concept of the invention is described more fully below with reference to the appended figures, which show embodiments of the concept of the invention. In the drawings, the size and relative sizes of the elements may be exaggerated for clarity reasons. Similar numbers refer to similar elements in all the drawings. However, this concept of the invention can be implemented in numerous different forms and should not be interpreted as being limited to the embodiments set out here. Rather, these embodiments are proposed in order that this description be complete, and communicate the scope of the concept of the invention to persons skilled in the art. The following embodiments are examined, for the sake of simplicity, in relation to the terminology and the structure of a device for holding and releasing an object, such as a medical implant.

With reference to the figures, a device 1 for holding and releasing an object 2 is shown.

In the example illustrated in the figures, said object 2 is a medical implant. The implant may or may not comprise a part that is movable with respect to another part of the implant. The medical implant may comprise a screw body 22 and a screw head 21. The screw head may be fixed with respect to the screw body 22 or movable, for example with a connection of the ball joint type. Thus, in the rest of the description, the device is described in connection with the implant 2, but the description also applies, of course, to any other object that is able to be held by the device and released.

The device may also be referred to as a gripper. Such a device can be used by an operator to handle an object by way of the device without touching the object with their fingers.

As described in detail below, the device in which the implant 2 is held also makes it possible to release the implant 2, which can then be extracted from the device for example with the aid of a suitable tool 9, for example a tool of the screwdriver type, having an end piece that is able to cooperate with the head 21 of the implant in order to couple the implant 2 to the tool 9.

Hook Systems

In the example illustrated in the figures, the device comprises two hook systems 11, 12 that make it possible to jointly hold the implant 2 before it is released.

The implant 2 is able to be coupled to the hook systems 11, 12 in order to be held in the device.

Each hook system 11, 12 may comprise an arm 110, 120 provided with at least one hook 13, 14 through which at least a part 22 of the implant 2 is able to extend.

At least one, preferably each, of the arms 110, 120 is movable so as to allow the corresponding hook system 11, 12 to be moved with respect to the other hook system 12, 11. According to one particular aspect, the one arm or each of the arms, and thus the one hook system or each of the hook systems, is/are movable by bending or elastic deformation. In other words, the operator can pinch the arm(s) in order to pivot or bend it/them toward one another.

The device makes it possible to release the implant by actuating the hook systems one-handedly with two fingers. The hook systems can be configured so as to allow such actuation of the hook systems equally well by a right-handed person and by a left-handed person. Provision may be made for the force to be applied to an arm or hook system in order to move it to be substantially the same in terms of value as the force to be applied to move the other arm or hook system so as to move the arms or hook systems toward one another.

The following description is given for an embodiment in which both arms or hook systems are movable, preferably by bending or elastic deformation, but the description also applies to the case in which only one arm or hook system is movable, preferably by bending or elastic deformation.

The movement of the arms or hook systems makes it possible to bring the hooks into a position allowing the implant to be coupled to the hooks in order to be held in the device by cooperation of the two hook systems or into a position releasing said implant.

According to one particular aspect, each hook system 11, 12 has at least one hook 13, 14 that exhibits a passage through which at least a part 22 of said object 2 is able to extend.

The hook system 12 may comprise an additional hook 15, through which at least a part 22 of said implant 2 is able to extend. The hook 15 is spaced apart from the hook 14 along the passage axis A14, A15 of the hook 14 or 15. The implant 2 is able to extend at least partly through these two hooks 14, 15.

When the implant 2 is engaged with the hook systems 11, 12, the hook 13 of the hook system 11 extends between the two hooks 14, 15 of the hook system 12.

Such a design of the hook systems 11, 12 in which one hook of a hook system is nested between two other hooks of the other hook system makes it possible to hold the implant 2 reliably. In particular, the risk of accidental releasing of the object caused by pivoting that would result from opposite return forces applied to the object is reduced.

Otherwise, as explained above, provision is made for an operator to be able to voluntarily release the implant 2 by applying a predefined pivoting force about an axis that is substantially orthogonal to the axis A2 of the implant 2 and is contained in a plane parallel to the mean plane in which the arms 110, 120 extend (or the mean plane of the body or of the cover).

Figure 9:
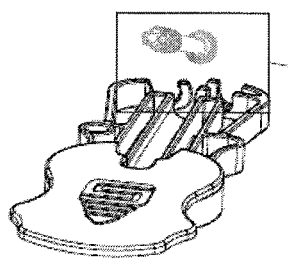
FIG. 9 is a perspective view of an assembly comprising an implant and a device according to one embodiment of the invention, in the state of the implant in which it has been removed from the device.
Figure 9A:
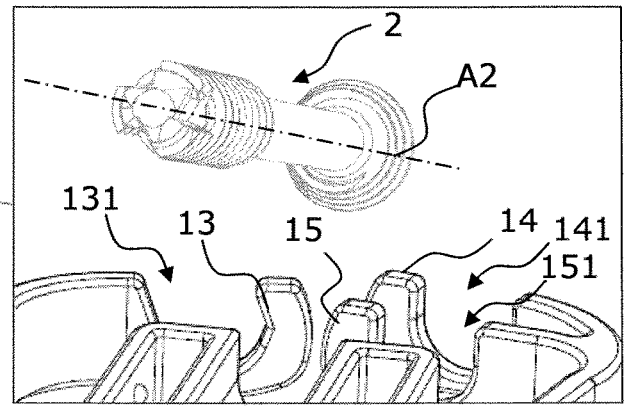
FIG. 9A is a detail view of FIG. 9.

As illustrated in FIG. 9A, each hook 13, 14, 15 has an opening 131, 141, 151, referred to as the insertion/releasing opening, defined between the base of the hook and the free end of the curved part thereof. Advantageously, each hook opening 131, 141, 151 exhibits more or less the same orientation as the opening of the or each other hook of the hook systems 11, 12.

The hook opening 131, 141, 151 may in particular be provided in a zone opposite to the zone of the hook in which the implant 2 rests when said implant 2 is coupled to the hook system 11, 12 and to the state in which the device is positioned on a horizontal surface. The openings of the hooks are thus situated above the zones in which the implant rests in the hooks.

In other words, when the operator holds the device in front of themselves, that is to say with the cover 190 (presented below) oriented toward themselves, the insertion/releasing openings of each hook are oriented substantially on the side facing the operator.

According to one embodiment, one 13 of the hooks has an end portion 138 the shape of which makes it possible to oppose any attempt to release the object 2 by movement in translation in a direction contained in a plane orthogonal to the axis A1 along which the implant 2 extends in the state in which the implant 2 is held by said hook systems 11, 12. In the held position of the implant 2, the axis A1 is substantially parallel to the passage axis A13, A14, A15 defined by the hooks.

According to one particular aspect, the end portion 138 of this hook 13 comprises a ramp 139 that makes it possible to prompt the releasing of the implant 2 by pivoting PIV2 the object 2 about an axis APIV2 orthogonal to the axis A1 along which said implant 2 is held by the hook systems 11, 12. The (virtual) axis APIV2 may be situated substantially at the level of the hook 14.

Provision may also be made for the operator to be able to remove the implant from the device by orienting the device with the implant downward such that when the operator moves one or each of the hook systems in order to release the implant, which then slides under the effect of gravity with respect for example to a receiving zone situated below the device. Provision may also be made for the operator to release the implant, without a particular inclination, by moving one or each of the hook systems and to extract the implant manually or with the aid of a tool (which may be coupled to the implant before it is released).

The screw head 21 protrudes from the assembly formed by the hooks 13, 14, 15, which partially surround the elongate screw body 22.

Body of the Device

As illustrated in the figures, the device comprises a body 10. The body 10 may have a longitudinal axis A10, which may be substantially parallel to the axis A1 presented below. Each arm 110, 120 has an end that is fixed to the body 10 of the device. The body 10 may extend at least partly between the two arms 110, 120. Each arm 110, 120 has another end provided with one hook 13 or a plurality of hooks 14, 15. As detailed above, provision may be made for each arm to be able to be moved, by bending or elastic deformation, toward the other arm.

The body may have a housing 100 for containing at least a part 22 of the implant 2. This housing 100 may have the form of an elongate groove along the axis of the body 10. The groove may comprise an end 101 for allowing the implant 2 to extend through this open end 101 in the housing 100.

The housing 100 may have another end 102 that is at least partially closed so as to prevent removal of the implant 2 through this other end 102.

When the operator activates the hook systems 11, 12 into the releasing position for example by pinching them so as to move them toward one another such that the hooks 13, 14, 15 no longer prevent the removal of the implant 2, the end zones of the hooks 13, 14, 15 may still serve as a support surface for the implant 2. If the device is inclined with the hooks 13, 14, 15 oriented upward with the hook systems 11, 12 in the releasing position, the implant could then slide under the effect of gravity. In this case, the implant 2 can be received in the housing 100 of the body 10, thereby avoiding the risk of the implant 2 falling onto the ground.

According to one particular aspect, the body 10 may also comprise at least one other housing for example for housing small implants (for example of the sealing screw for a dental implant type). Thus, in the example illustrated in the figures, in particular in FIG. 4, the body comprises two other housings 103, 104, one 103 in the shape of a circle and the other 104 in the overall shape of a droplet.

In the example illustrated in the figures, the free end 221 of the screw body at the opposite end from the screw head 21 extends in the main body 10 of the device, preferably in the housing 100 provided in the main body for receiving said end.

The housing 100 thus makes it possible to guide any slipping of the implant 2 in the main body 10 of the device. Provision may also be made for the screw head to be designed so as to be able to butt against a hook.

The fact that the end of the screw body extends in the housing 100 also makes it possible to limit the risk of damage to the surroundings of the device. In particular, the risk of perforation of a sachet, potentially under vacuum, which could contain the device is reduced since the end of the screw body is protected by the main body of the device.

As explained above, the body 10 of the device may also make it possible to accommodate one or more other objects. The device may be configured to allow or not allow access to the housing(s) 103, 104 depending on the position of the cover 190 (presented below). As detailed above, it is thus possible to provide for the body 10 to comprise one or more housings for one or more parts and for this or these housings to be closed by the cover in the concealing position of the cover, and optionally in an intermediate position of the cover in which this or these housings remain concealed while the implant and/or the hook systems is/are sufficiently uncovered by the cover so as to allow the implant to be released. The operator can then continue to move the cover until the housing(s) 103, 104 is/are uncovered.

Cover

The device may comprise a cover 190 mounted so as to slide between a position, referred to as the concealing position, which at least partially conceals the hook systems 11, 12, and another position, referred to as the position for accessing the hook systems, which allows the operator to move the hook systems 11, 12. Provision may be made for the housing(s) 103, 104, in the position for accessing the hook systems, to remain concealed and for the operator to need to continue moving the cover in order to access this or these housings 103, 104.

To this end, the device may comprise a sliding system. The sliding system may comprise lugs or ribs provided on the cover, which fit in slideways, formed for example by slots in the body 10, preferably on either side of the housing 100. As mentioned above, the sliding system makes it possible to obtain, in addition to the closed concealing position and the position for accessing the hook systems, an additional open position by continuing the sliding (descent) of the cover in order to access one or more additional housings such as the housings 103 and 104.

It should be noted that the cover 190 in the concealing position (closed position) prevents accidental releasing of the implant. The cover makes it possible to prevent or impede access for the operator to the hook systems so as to prevent accidental releasing of the object by unintentional displacement of the hook systems or by rocking by unintentional pivoting about the (virtual) axis APIV2 illustrated in FIG. 8A.

In the normal position for grasping of the device by the operator, that is to say in top view of the device and in the concealing position of the cover, at least a part of the hook systems is concealed by the cover 190.

The cover 190 may be configured such that, in the concealing position, the length of the implant, that is to say at least the head and threaded end thereof, remains visible. The length of the implant may thus remain visible at least to the operator looking at the device from above in the normal configuration for grasping the device.

Figure 2:
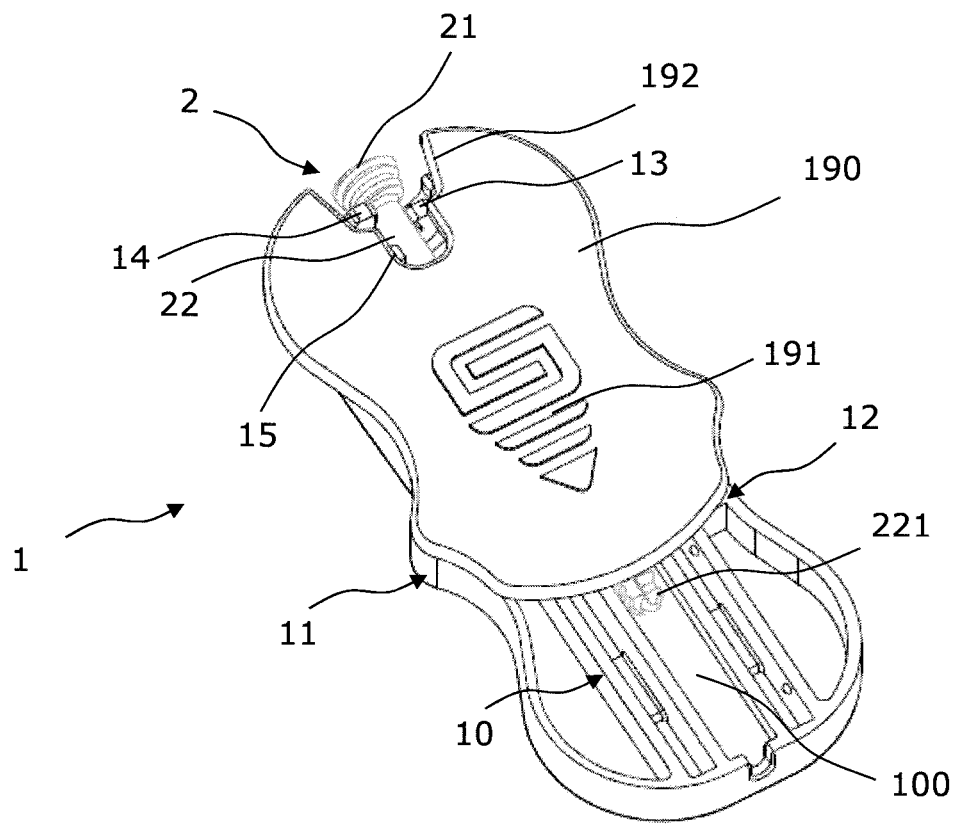
FIG. 2 is a view according to one embodiment of a holding device and of an implant held in the device by hook systems, the device comprising a cover in the closed/concealing position.
Figure 3:
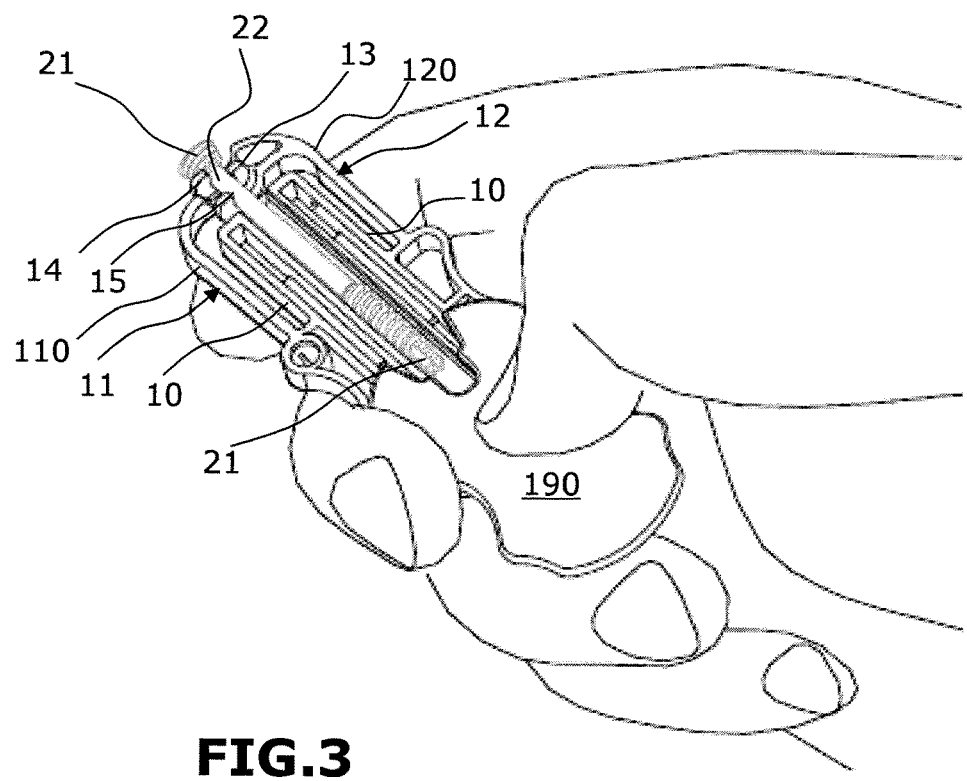
FIG. 3 is a view corresponding to the device in FIG. 2 in an open position of the cover.

In particular, the cover has a cutout or clearance 192, which makes it possible to see a part of the implant end, for example the screw head 21 and the start of the screw body 22 in the example illustrated in FIG. 2.

The cover 190 is provided with a zone 191 for positioning a finger, also referred to as an impression, for example comprising recessed or raised surface irregularities such as ribs or striations, which make it easier for the operator to slide the cover.

Return Forces

Figure 7:
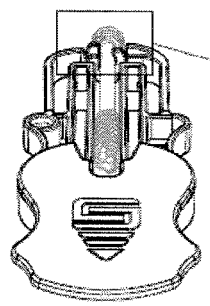
FIG. 7 is a view of an assembly comprising a device and an implant according to one embodiment of the invention, the implant being engaged with the hooks subjected to return forces.
Figure 7A:
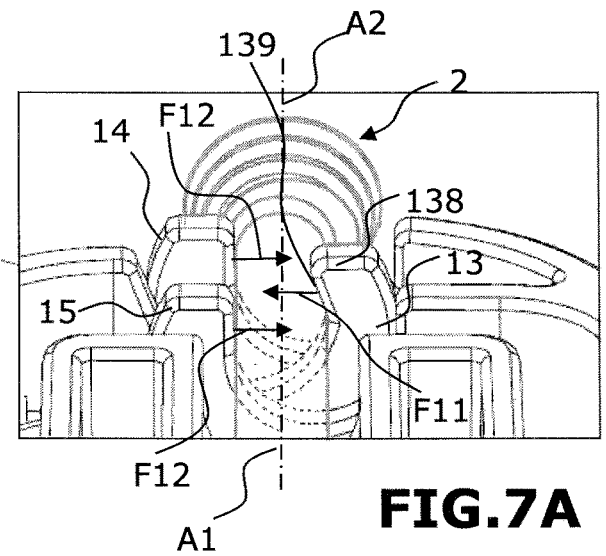
FIG. 7A is a detail view of FIG. 7.

As illustrated in FIG. 7A, when the implant 2 is held in the device by being coupled to the hook systems 11, 12, the or each hook of a hook system 11, 12 is subjected to a return force F11, F12 that tends to move it in the opposite direction to the direction of the return force F12, F11 to which the or each hook of the other hook system 12, 11 is subjected. It is also possible to provide for only one of the hook systems to be movable and to be subjected to a return force when the implant is engaged with the hook systems. The features presented in the description, in particular below, also apply to such an embodiment.

The implant 2 is kept coupled to said hook systems 11, 12 under the effect of the return forces F11, F12 applied in opposite directions to the object 2 by the hooks of said hook systems 11, 12.

The opposing return forces to which the implant 2 is subjected on account of its being coupled to the hooks 13, 14, 15 of the hook systems 11, 12 make it possible to hold the object inside the hooks 13, 14, 15 of the hook systems 11, 12.

When the implant 2 is engaged with the hooks 13, 14, 15 of the hook systems, the passage axes A13, A14, A15 of the hooks are substantially parallel and optionally coaxial. In particular, the axes A13, A14, A15 are then substantially parallel to the axis A1 along which the implant 2 is held in the device. This axis A1 is substantially coincident with the axis A2 of the implant 2 in the example illustrated in the figures.

According to one particular aspect, the return forces F11, F12 are elastic return forces.

Thus, when the part 22 of the implant 2 extends through the hooks 13, 14, 15, the hook 13 and the hooks 14, 15 tend to pull on the part 22 of the implant in opposite directions on account of the return forces F11, F12 to which said hooks 13 and 14, 15 are subjected. The implant is thus held in position through the hooks by cooperation of the hooks with the implant.

The upper shape of a hook, for example of the hook 14, may have a suitable shape, preferably with a noncircular section, for example with cut facets, in order to cooperate with a shape of the implant so as to limit or prevent the rotation of the implant itself about the axis of its body or of a part of the implant, in the case of an implant having a movable part. It is thus possible to provide, in the case of a screw head mounted by way of a ball-joint connection on its screw body, for the screw head, which causes the hooks to protrude, to be prevented from rotating with respect to its body by virtue of a particular shape of the hook 14 with which the screw head can cooperate.

The hook(s) of each of the hook systems 11, 12 is configured to be able to be moved with respect to the or each hook of the other hook system 12, 11 into a position, referred to as the releasing position, that makes it possible to release the object from the hook systems 11, 12.

The hooks 13, 14, 15 are configured to be moved into a position with respect to one another that makes it possible to release the implant from the hooks.

The releasing position may be obtained by moving at least one, preferably each, of the hook systems 11, 12 in an opposite direction to the return force to which said hook system 11, 12 is subjected.

Specifically, the operator can use their fingers to press on the hook systems 11, 12 so as to move them toward one another by acting counter to the return forces of the hook systems.

Figure 4:
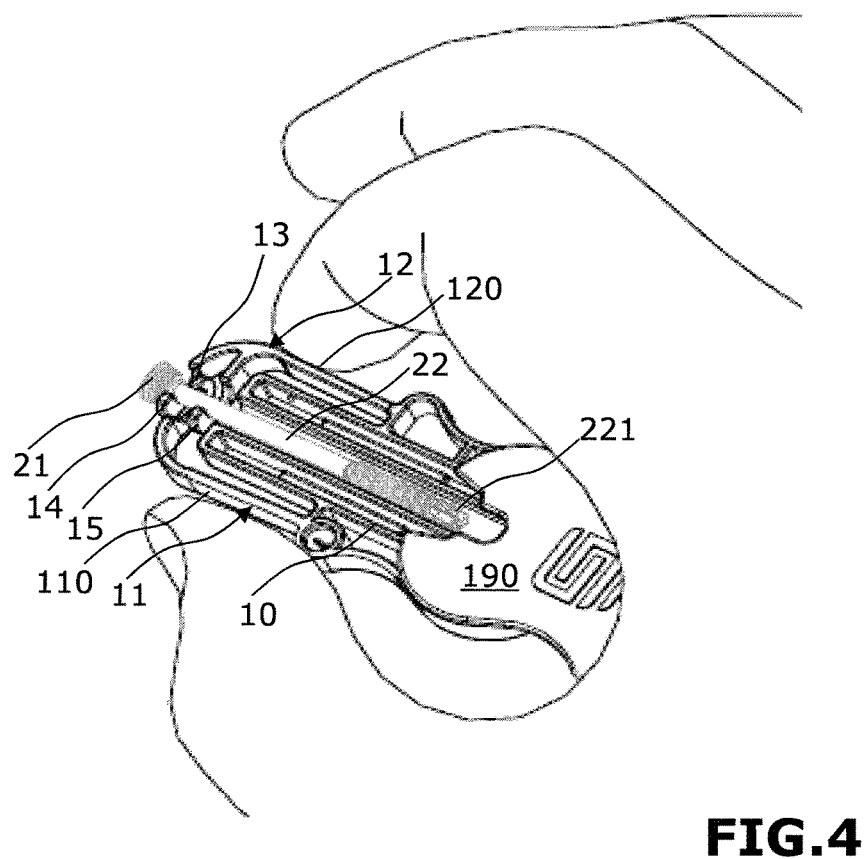
FIG. 4 is a view of a device and of an implant according to one embodiment, showing an operator pinching the hook systems with two fingers in order to release the implant.
Figure 5:
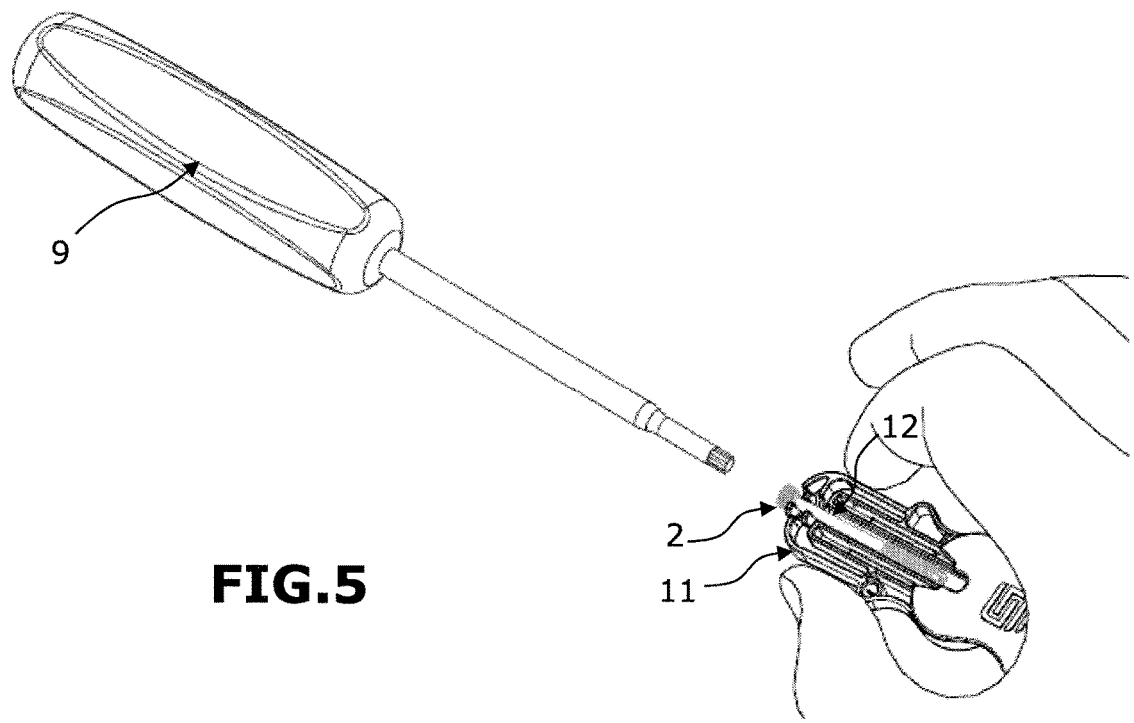
FIG. 5 is a view according to one embodiment of a holding device and of a medical implant, a tool being introduced so as to be coupled to the implant and, preferably after the hook systems have been pinched, extract the implant from the device for example by the implant being moved axially.
Figure 6:
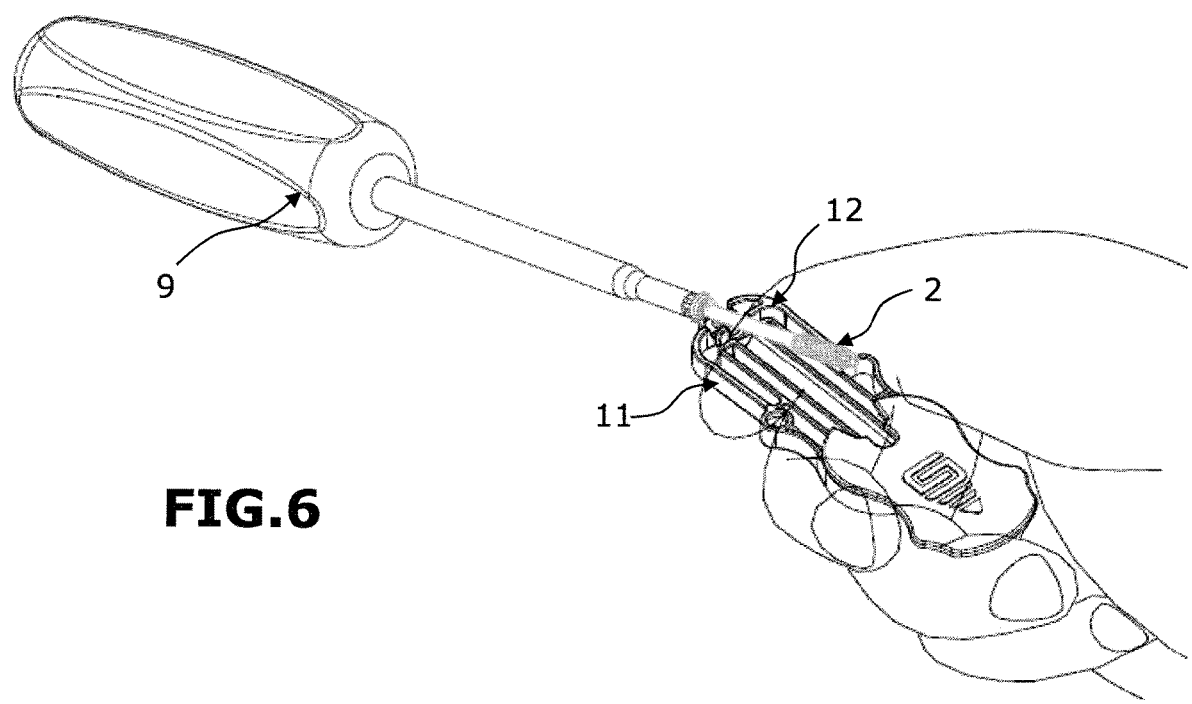
FIG. 6 is a view according to one embodiment of a holding device and of a medical implant, in the open position of the cover, a tool being introduced so as to release the implant from the device by pivoting.

In particular, the operator can move the arms 110, 120 of the hook systems 11, 12 toward one another by pinching said arms between two fingers, as illustrated in FIGS. 4 and 5.

In the case of one of the hook systems not being movable, said hook system then being referred to as fixed, it is possible to provide for the operator to release the implant by moving the other hook system in the direction toward the fixed hook system.

Figure 8:
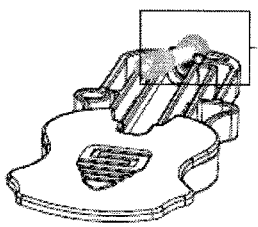
FIG. 8 is a view of the device and of the implant according to one embodiment of the invention, while the implant is being released by being pivoted about an axis orthogonal to the axis of the implant and parallel to the mean plane of the cover.
Figure 8A:
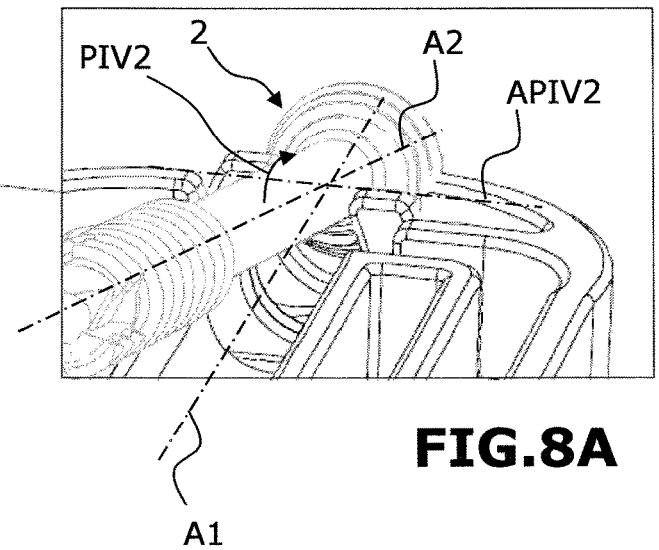
FIG. 8A is a detail view of FIG. 8.

It is also possible to provide, as illustrated in FIG. 8, for the implant to be able to be removed by pivoting the implant, for example about a virtual axis or point situated at the level of the hook 14, without it being necessary to press or apply a force counter to the return force of the hook systems 11, 12.

A device as described above makes it possible to release the implant 2 in the following way. The operator moves the cover 190 to allow access to the hook systems 11, 12. Then, the operator releases the object 2.

The object can be released by moving at least a part of the hooks 13, 14, 15 by applying a force in a direction opposite to the return force to which they are subjected on account of the flexibility of the arms 110, 120.

Preferably, the tool 9 is coupled to the implant before it is released, so as to benefit from the holding of the implant 2 in the device 1, in order for it not to be necessary to manually touch the implant. The tool 9 can then be used to remove the implant for example by axial movement along A2.

As a variant, if, in a given use context, manually touching the implant does not have a negative effect, the operator can then simply release the implant by moving one or the hook systems, manually taking hold of it. It is also possible to provide for the operator to be able to slide the released implant out of the device.

The object can also be released by pivoting the object 2 about a (virtual) axis APIV2 transverse to the axis, referred to as the passage axis A1 along which the object 2 extends.

Pivoting can be effected manually or with the aid of a tool 9.

Where reference is made, throughout the specification, to "one/an embodiment", this means that a particular functionality, structure or feature described in relation to one embodiment is included in at least one embodiment of the present invention. Thus, the appearance of the expression "in one embodiment" at various points throughout the specification does not necessarily refer to one and the same embodiment. Moreover, the particular functionalities, structures or features can be combined in any appropriate way in one or more embodiments.

The invention is not limited to the embodiments illustrated in the drawings.

In addition, the term "comprising" does not exclude other elements or steps.

Moreover, features or steps that have been described with reference to one of the embodiments set out above can also be used in combination with other features or steps of other embodiments set out above.

The invention claimed is:

1. A device for holding and releasing an object, such as a medical implant, comprising:
    two hook systems to which said object is able to be coupled so as to allow said hook systems to jointly hold said object,
    said two hook systems being configured such that, in the state in which said object is coupled to said hook systems, at least one of the hook systems is subjected to a return force that makes it possible to keep the object coupled to said hook systems;
    in that each hook system has at least one hook that exhibits a passage through which at least a part of said object is able to extend,
    and in that, with said passage of said at least one hook of each hook system having a passage axis along which at least a part of said object is able to extend, said at least one hook of each hook system exhibits a hook opening zone configured so as to allow said object to be released through said hook opening zone, by said object being pivoted about an axis orthogonal to the passage axis,
    each of said two hook systems comprises an arm that is provided with at least one hook,
    wherein said arm is movable so as to allow the corresponding hook system to be moved with respect to another of said two hook systems;
    wherein the two hook systems are activable by the operator into the releasing position by pinching the arms of the hook systems so as to move said arms toward one another such that the hooks no longer prevent the removal of the implant.

2. The device as claimed in claim 1, wherein, in the state in which said object is coupled to said hook systems, each of said hook systems is subjected to a return force,
    said hook systems being configured such that the return force to which one of said hook systems is subjected tends to move it in the opposite direction to the direction of the return force to which another of said two hook systems is subjected, the object being kept coupled to said hook systems under the return forces applied in opposite directions to the object by said hook systems.

3. The device as claimed in claim 1, wherein at least one, preferably each, of the hook systems is configured to be able to be moved with respect to another of said two hook systems into a position, referred to as the releasing position, that makes it possible to release the object from the hook systems.

4. The device as claimed in claim 1, wherein the device comprises a body to which each hook system is coupled.

5. The device as claimed in claim 1, wherein the hooks are distributed, in the state in which the object is coupled to said hook systems, at different positions along said passage axis.

6. The device as claimed in claim 1, wherein said or each hook system is movable by bending about an axis orthogonal to said passage axis.

7. The device as claimed in claim 1, at least one of the hooks has an end portion that extends in such a way that, when the object is coupled to the hook systems by being subjected to the return force of the hook system or each of the hook systems, said end portion opposes releasing of the object by movement in translation in a direction contained in a plane orthogonal to the passage axis along which the object extends in the state in which the object is held by said hook systems.

8. The device as claimed in claim 1, wherein the device also comprises a cover mounted so as to slide between a position, referred to as the concealing position, which at least partially conceals the hook systems, and another position, referred to as the position for accessing the hook systems, which allows the operator to move the hook systems.

9. The device as claimed in claim 8, wherein the object having opposite ends, the cover is configured such that, in the concealing position, at least the opposite ends of the object thereof, remains visible.

10. An assembly comprising a device as claimed in claim 1, said assembly further comprising an object held by said hook systems.

11. The assembly as claimed in claim 10, wherein said object, preferably a medical implant, comprises an elongate screw body and a screw head, the hook systems engaging with the elongate screw body.

12. The assembly as claimed in claim 11, wherein the end of the screw body is contained in a housing provided in a body of the device.

13. A method for releasing an object coupled to an assembly as claimed in claim 10, said method comprising the following steps:
    when a cover is present, moving the cover so as to allow access to the hook systems and/or to uncover a part of the object previously concealed by the cover;
    releasing the object by:
    i) moving at least one, preferably each, of the hook systems by applying a force to at least one, preferably each, of the hook systems in a direction opposite to the return force of said hook system, or ii) pivoting the object about an axis transverse to the passage axis, along which the object extends, said pivoting being effected preferably with aid of a tool coupled to the object.

14. The device as claimed in claim 1, wherein one of the hook systems comprises an additional hook, through which at least a part of said object is able to extend, said at least one hook of another of said two hook systems being able to extend, in the state in which the object is coupled to the hook systems, between the two hooks of said hook system.

* * * * *